US012784201B2

(12) United States Patent
Watanabe et al.

(10) Patent No.: US 12,784,201 B2
(45) Date of Patent: Nov. 3, 2026

(54) INFORMATION PROCESSING APPARATUS, INFORMATION PROCESSING METHOD, MEDICAL IMAGE IDENTIFICATION DEVICE, AND NON-TRANSITORY COMPUTER READABLE MEDIUM STORING PROGRAM

(71) Applicant: NEC Corporation, Tokyo (JP)

(72) Inventors: Kazuhiro Watanabe, Tokyo (JP); Akinori Ebihara, Tokyo (JP); Taiki Miyagawa, Tokyo (JP)

(73) Assignee: NEC CORPORATION, Tokyo (JP)

(*) Notice: Subject to any disclaimer, the term of this patent is extended or adjusted under 35 U.S.C. 154(b) by 400 days.

(21) Appl. No.: 18/567,102

(22) PCT Filed: Jun. 9, 2021

(86) PCT No.: PCT/JP2021/021954

§ 371 (c)(1),
(2) Date: Dec. 5, 2023

(87) PCT Pub. No.: WO2022/259429

PCT Pub. Date: Dec. 15, 2022

(65) Prior Publication Data

US 2024/0265536 A1 Aug. 8, 2024

(51) Int. Cl.
*G06T 7/00* (2017.01)
*G06V 10/764* (2022.01)
(Continued)

(52) U.S. Cl.
CPC .......... *G06T 7/0012* (2013.01); *G06V 10/764* (2022.01); *G16H 30/40* (2018.01); *G16H 50/20* (2018.01); *G06T 2207/30096* (2013.01)

(58) Field of Classification Search
None
See application file for complete search history.

(56) References Cited

U.S. PATENT DOCUMENTS

2002/0174086 A1* 11/2002 Verma .................. G06F 18/256
2010/0183210 A1* 7/2010 Van Uitert ............ G06T 7/0012
382/131

(Continued)

FOREIGN PATENT DOCUMENTS

JP 2001-523824 A 11/2001
JP 2008-299589 A 12/2008

(Continued)

OTHER PUBLICATIONS

Extended European Search Report for EP Application No. 21945105.1, dated on May 15, 2024.

(Continued)

*Primary Examiner* — SJ Park

(57) ABSTRACT

According to one example embodiment, an information processing apparatus includes: an acquisition unit configured to sequentially acquire a plurality of elements included in sequential data; a first calculation unit configured to calculate, based on two or more of the plurality of elements, an indicator indicating which one of a plurality of classes each of the plurality of elements should belong to; a second calculation unit configured to calculate weights showing importance of the respective indicators of the plurality of respective elements; a third calculation unit configured to weight the indicators of the plurality of respective elements by the corresponding weights and integrate the weighted indicators to calculate an integrated indicator indicating which one of the plurality of classes the sequential data should belong to; and a classification unit configured to classify the sequential data into one of the classes based on the integrated indicator.

9 Claims, 5 Drawing Sheets

(51) Int. Cl.
*G16H 30/40* (2018.01)
*G16H 50/20* (2018.01)

(56) References Cited

U.S. PATENT DOCUMENTS

| | | | | |
|---|---|---|---|---|
| 2014/0219518 | A1* | 8/2014 | Yamazaki | G06V 40/168 382/118 |
| 2020/0365268 | A1 | 11/2020 | Michuda et al. | |

FOREIGN PATENT DOCUMENTS

| | | | |
|---|---|---|---|
| JP | 2009-245314 | A | 10/2009 |
| JP | 2010-170280 | A | 8/2010 |
| WO | 2020/194497 | A1 | 10/2020 |

OTHER PUBLICATIONS

Diyan Teng et al., "Wald-Kernel: Learning to Aggregate Information for Sequential Inference", arXiv.org, Cornell University Library, 201 Olin Library Cornell University Ithaca, NY 14853, Aug. 31, 2015, pp. 1-14.

International Search Report for PCT Application No. PCT/JP2021/021954, mailed on Sep. 7, 2021.

* cited by examiner

INFORMATION PROCESSING APPARATUS, INFORMATION PROCESSING METHOD, MEDICAL IMAGE IDENTIFICATION DEVICE, AND NON-TRANSITORY COMPUTER READABLE MEDIUM STORING PROGRAM

This application is a National Stage Entry of PCT/JP2021/021954 filed on Jun. 9, 2021, the contents of all of which are incorporated herein by reference, in their entirety.

TECHNICAL FIELD

The present invention relates to an information processing apparatus, an information processing method, a medical image identification device, and a non-transitory computer readable medium storing a program.

BACKGROUND ART

Patent Literature 1 to 4 disclose information processing techniques using a Sequential Probability Ratio Test (SPRT). SPRT is a kind of method of determining which one of a plurality of predetermined classes sequential data input sequentially belongs to.

CITATION LIST

Patent Literature

[Patent Literature 1] Japanese Unexamined Patent Application Publication No. 2009-245314
[Patent Literature 2] Japanese Unexamined Patent Application Publication No. 2008-299589
[Patent Literature 3] Published Japanese Translation of PCT International Publication for Patent Application, No. 2001-523824
[Patent Literature 4] International Patent Publication No. WO 2020/194497

SUMMARY OF INVENTION

Technical Problem

In the mathematical formulae used for SPRT as disclosed in Patent Literature 1 to 4, it is assumed that the respective importance for the determination of all the elements of the input sequential data are equal to each other. Therefore, depending on the property of the sequential data, it is possible that a sufficiently high accuracy cannot be achieved.

The present disclosure has been made in order to solve the aforementioned problem, and aims to provide an information processing apparatus, an information processing method, a medical image identification device, and a non-transitory computer readable medium storing a program capable of accurately classifying sequential data.

Solution to Problem

An information processing apparatus according to the present disclosure includes: acquisition means for sequentially acquiring a plurality of elements included in sequential data; a first calculation means for calculating, based on two or more of the plurality of elements, indicators indicating which one of a plurality of classes the plurality of respective elements should belong to: a second calculation means for calculating weights showing importance of the respective indicators of the plurality of respective elements; a third calculation means for weighting the indicators of the plurality of respective elements by the corresponding weights and integrating the weighted indicators to calculate an integrated indicator indicating which one of the plurality of classes the sequential data should belong to; and classification means for classifying the sequential data into one of the classes based on the integrated indicator.

An information processing method according to the present disclosure includes the steps of: sequentially acquiring a plurality of elements included in sequential data; calculating, based on two or more of the plurality of elements, indicators indicating which one of a plurality of classes the plurality of respective elements should belong to: calculating weights showing importance of the respective indicators of the plurality of respective elements; weighting the indicators of the plurality of respective elements by the corresponding weights and integrating the weighted indicators to calculate an integrated indicator indicating which one of the plurality of classes the sequential data should belong to; and classifying the sequential data into one of the classes based on the integrated indicator.

A non-transitory computer readable medium according to the present disclosure stores a program for causing a computer to execute an information processing method including the steps of: sequentially acquiring a plurality of elements included in sequential data; calculating, based on two or more of the plurality of elements, indicators indicating which one of a plurality of classes the plurality of respective elements should belong to: calculating weights showing importance of the respective indicators of the plurality of respective elements; weighting the indicators of the plurality of respective elements by the corresponding weights and integrating the weighted indicators to calculate an integrated indicator indicating which one of the plurality of classes the sequential data should belong to; and classifying the sequential data into one of the classes based on the integrated indicator.

Advantageous Effects of Invention

According to the present disclosure, it is possible to provide an information processing apparatus, an information processing method, a medical image identification device, and a non-transitory computer readable medium storing a program capable of accurately classifying sequential data.

EXAMPLE EMBODIMENT

Hereinafter, with reference to the drawings, illustrative example embodiments of the present invention will be described. Throughout the drawings, the same components or corresponding components are labeled with the same references, and the description thereof may be omitted or simplified.

First Example Embodiment

A sequential data classification system according to the present example embodiment will be described. The sequential data classification system of the present example embodiment is a system for classifying sequential data into one of a plurality of predetermined classes by sequentially acquiring and analyzing a plurality of elements included in the sequential data.

Here, the sequential data means a data sequence that can be decomposed into a plurality of elements. The sequential data may be time-series data or non-time-series data. Specific examples of the time-series data include, for example, moving image data and audio data. Specific examples of the non-time-series data include vegetation data sampled from a plurality of locations, inspection data of a plurality of parts of a product, and a plurality of biometric data for biometric authentication. When the sequential data is moving image data, the plurality of elements included in the sequential data may be a plurality of images (frames) constituting the moving image. When the sequential data is inspection data of a plurality of parts of a product, the plurality of elements included in the sequential data may be inspection data of each part of the product. Note that sequential data and elements to which classification processing of the present example embodiment can be applied are not limited to them.

When the sequential data is inspection data of a plurality of parts of a product, the class classified by the sequential data classification system of the present example embodiment may be, for example, a first class indicating that the product is a non-defective product and a second class indicating that the product is a defective product. When the sequential data is a plurality of images (frames) forming medical data, the class classified by the sequential data classification system of the present example embodiment may be, for example, a first class indicating that an image includes a cancerous site, and a second class indicating that an image does not include a cancerous site. The number of classes may be three or more.

Figure 1:
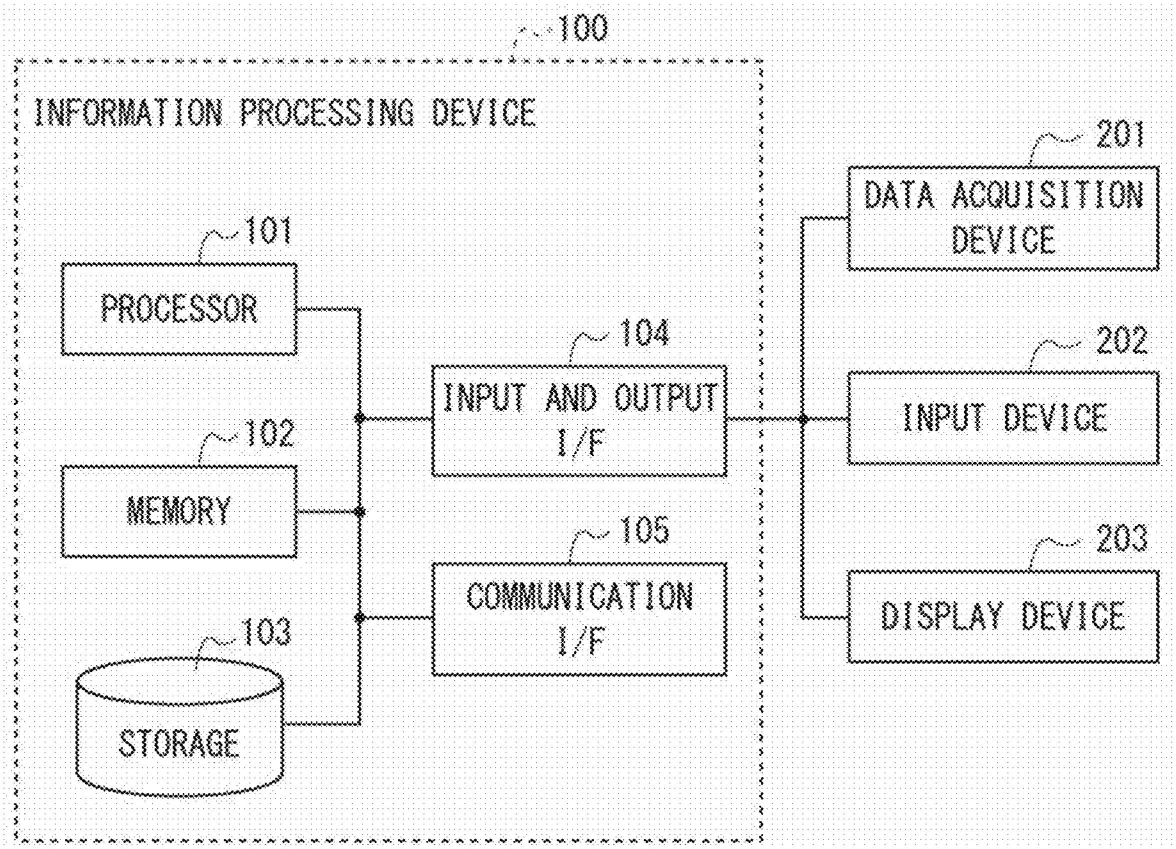
FIG. 1 is a schematic diagram illustrating an overall configuration of a sequential data classification system according to a first example embodiment.

FIG. 1 is a schematic diagram illustrating an overall configuration of a sequential data classification system according to the present example embodiment. FIG. 1 illustrates a hardware configuration included in the sequential data classification system. The sequential data classification system includes an information processing device 100, a data acquisition device 201, an input device 202, and a display device 203.

The information processing device 100 is a computer such as a cellular phone, a smartphone, a desktop personal computer (PC), a laptop PC, or a server. The information processing device 100 includes a processor 101, a memory 102, a storage 103, an input and output interface (I/F) 104, and a communication I/F 105. The units of the information processing device 100 are mutually connected via a bus, wiring, driving device, and the like, and can mutually transmit and receive control signals and data.

The processor 101 is, for example, an arithmetic processing device such as a central processing unit (CPU) or a graphics processing unit (GPU). The memory 102 is a volatile or non-volatile storage medium such as a random access memory (RAM) or a read only memory (ROM). The storage 103 is a non-volatile storage medium such as a hard disk drive (HDD), a solid state drive (SSD), or a memory card.

The memory 102 or the storage 103 stores a program for implementing an information processing function of the information processing device 100. When executing the above-described program, the processor 101 may read the program into the memory 102 and then execute the program, or may execute the program without reading the program into the memory 102.

The above-described program may be stored using various types of non-transitory computer-readable media and supplied to the information processing device 100. Non-transitory computer-readable media include storage media in various types of forms. Non-transitory computer-readable media include, for example, a magnetic storage medium, a magneto-optical storage medium, an optical storage medium, and a semiconductor memory.

Examples of the magnetic storage medium include a flexible disk, a magnetic tape, and a hard disk drive. Examples of magneto-optical storage media include a magneto-optical disk. Example of an optical storage medium are compact disc read only memory (CD-ROM), compact disc recordable (CD-R), and compact disc rewritable (CD-R/W). Examples of the semiconductor memory include a mask ROM, a programmable ROM (PROM), an erasable PROM (EPROM), a flash ROM, and a RAM.

Alternatively, the program may be supplied to the information processing device 100 via various types of transitory computer-readable media. Transitory computer-readable media include, for example, electrical signals, optical signals, and electromagnetic waves. The transitory computer-readable media may supply the program to the information processing device 100 via a wired communication path such as an electric wire or an optical fiber or a wireless communication path.

The input and output I/F 104 is a communication interface for communicating with peripheral devices based on standards such as universal serial bus (USB) and digital visual interface (DVI). The input and output I/F 104 can perform wired or wireless communication connection with the data acquisition device 201, the input device 202, and the display device 203. Thus, the information processing device 100 can transmit and receive data and control signals to and from the data acquisition device 201, the input device 202, and the display device 203.

The communication I/F 105 is a communication interface based on a standard such as Bluetooth (registered trademark), Wi-Fi (registered trademark), or 4G. The communication I/F 105 can perform a wired or wireless communication connection to an external device. Thus, the information processing device 100 can transmit and receive data to and from an external apparatus.

The data acquisition device 201 is a device for acquiring sequential data. For example, when the sequential data is inspection data of a product, the data acquisition device 201 may be an inspection device provided in a factory or the like. For example, when the sequential data is biometric data for biometric authentication, the data acquisition device 201 may be a device for acquiring biometric information such as a digital camera, a microphone, or a fingerprint collection scanner. When, for example, the sequential data is medical data for lesion detection, the data acquisition device 201 may be a device for acquiring medical information, such as an endoscope system, a Magnetic Resonance Imaging (MRI) system, or a Computed Tomography (CT) system. When the data acquisition device 201 includes a device such as a sensor that acquires an analog signal, the data acquisition device 201 may include an analog-to-digital conversion (AD conversion) device that converts the analog signal into digital data. The sequential data acquired by the data acquisition device 201 is input to the information processing device 100.

The input device 202 is a user interface for receiving an operation of the information processing device 100 by a user. Examples of the input device 202 include a keyboard, a mouse, a trackball, a touch sensor, a pen tablet, a button, and the like. The display device 203 is a device that displays a screen based on drawing data processed by the processor 101. Examples of the display device 203 include a liquid crystal display (LCD), a cathode ray tube (CRT) display, and an organic light emitting diode (OLED) display. The input device 202 and the display device 203 may be integrally formed as a touch panel.

Note that the hardware configuration illustrated in FIG. 1 is an example, and other devices may be added or some of the devices may not be provided. Further, some devices may be replaced by other devices having similar functions. Further, some functions of the present example embodiment may be provided by another device via a network, or the functions of the present example embodiment may be implemented by being distributed among a plurality of devices. For example, the storage 103 may be replaced by a cloud storage external to the information processing device 100. When the acquisition of the sequential data is performed in a system different from the sequential data classification system, the data acquisition device 201 may be omitted. Alternatively, the data acquisition device 201, the input device 202, or the display device 203 may be provided in the information processing device 100. Thus, the hardware configuration illustrated in FIG. 1 can be changed as appropriate.

Figure 2:
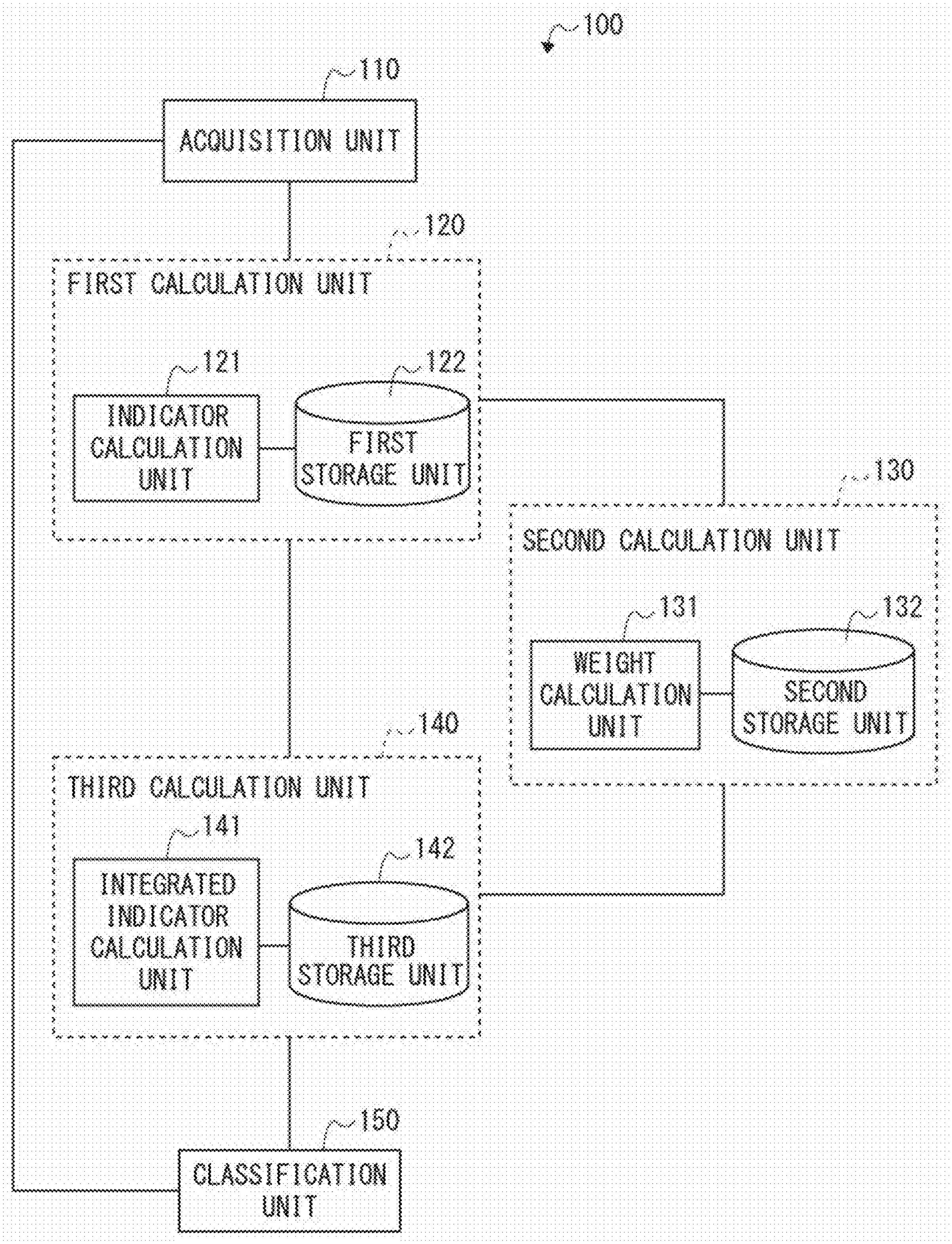
FIG. 2 is a functional block diagram of an information processing apparatus provided in the sequential data classification system according to the first example embodiment.

FIG. 2 is a functional block diagram of the information processing apparatus 100 according to this example embodiment. The information processing apparatus 100 includes an acquisition unit 110, a first calculation unit 120, a second calculation unit 130, a third calculation unit 140, and a classification unit 150. The first calculation unit 120 includes an indicator calculation unit 121 and a first storage unit 122. The second calculation unit 130 includes a weight calculation unit 131 and a second storage unit 132. The third calculation unit 140 includes an integrated indicator calculation unit 141 and a third storage unit 142.

The processor 101 executes a program stored in the memory 102, the storage 103, or the like, thereby implementing the functions of the acquisition unit 110, the indicator calculation unit 121, the weight calculation unit 131, the integrated indicator calculation unit 141, and the classification unit 150. Further, the processor 101 controls the storage 103 based on the program, thereby implementing the functions of the first storage unit 122, the second storage unit 132, and the third storage unit 142. Specific processing performed by these units will be described later.

Figure 3:
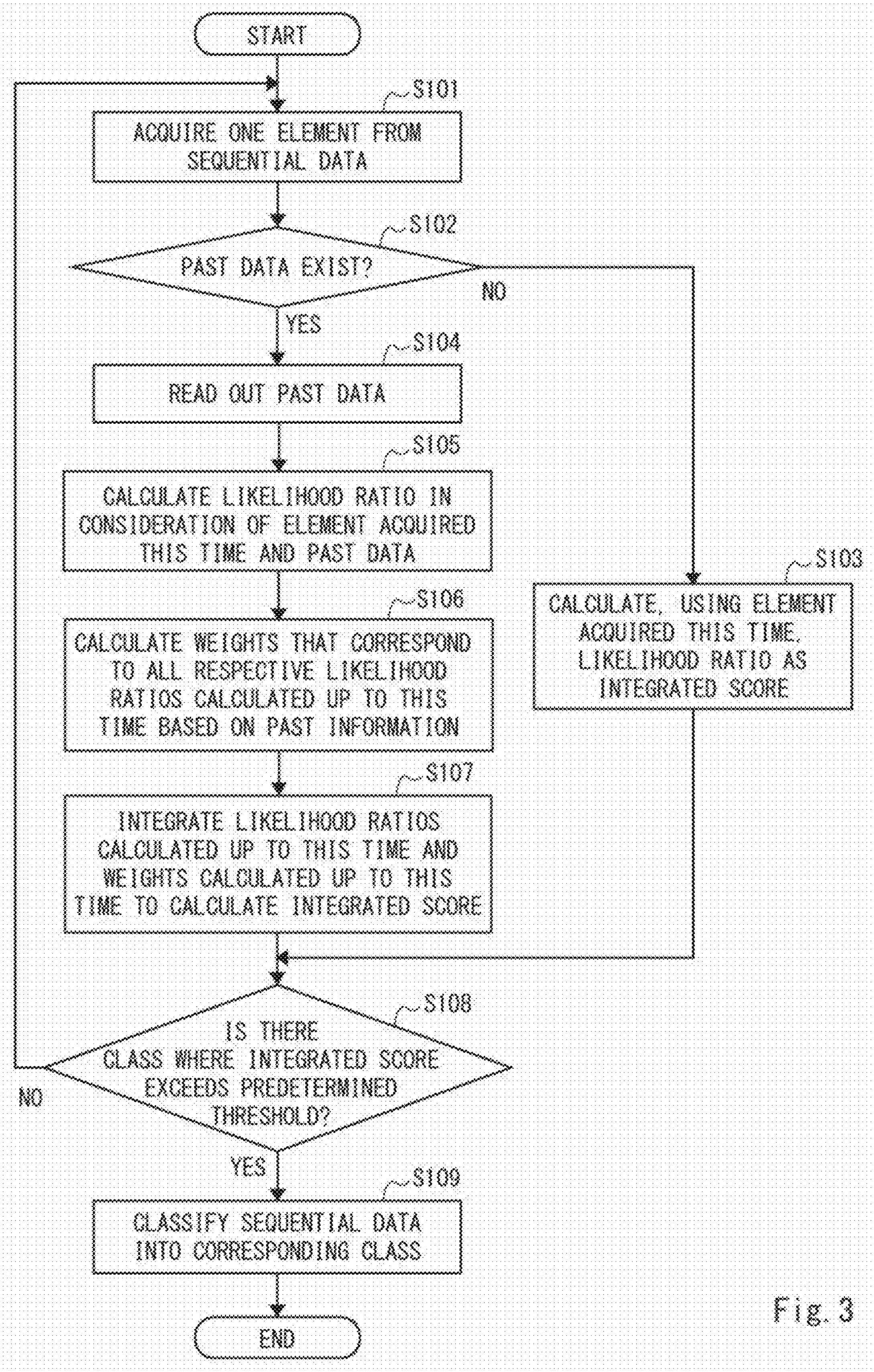
FIG. 3 is a flowchart illustrating an example of classification processing performed by an information processing apparatus according to the first example embodiment.

FIG. 3 is a flowchart illustrating an example of classification processing performed by the information processing device 100 according to the present example embodiment. The classification processing illustrated in FIG. 3 is a process of classifying input sequential data into one of a plurality of predetermined classes. The classification processing of FIG. 3 includes a loop process (Steps S101 to S107) in which elements are acquired one by one from sequential data including a plurality of elements and an integrated indicator is sequentially calculated. This loop process is repeated until the class of the classification destination of the sequential data is determined based on the integrated indicator.

The process of FIG. 3 may be started, for example, when a predetermined user operation is performed on the input device 202. However, the start timing of the process is not limited to this. For example, the process of FIG. 3 may be executed when the sequential data is input from the data acquisition device 201. When sequential data is continuously input as in the case where the data acquisition device 201 is a surveillance camera, the process of FIG. 3 may be repeatedly executed at predetermined time intervals.

In step S101, the acquisition unit 110 acquires one element of the sequential data. The acquisition processing at this time may be a process of directly acquiring data from the data acquisition device 201, or a process of reading out data acquired from the data acquisition device 201 and stored in the storage 103 or the like in advance. After that, the process proceeds to Step S102.

In Step S102, the indicator calculation unit 121 refers to the first storage unit 122, and determines the presence or absence of past data. The past data includes, for example, elements acquired in the past, and a result of performing processing (an indicator, such as a likelihood ratio) by the indicator calculation unit 121 on one or more elements including this element that have been acquired in the past.

When, for example, there is no past data in Step S102 (NO in Step S102), the process proceeds to Step S103. In Step S103, the indicator calculation unit 121 calculates, in consideration of the first element of the sequential data, an indicator indicating which one of the plurality of classes the input element should belong to. The first calculation unit 120 outputs the calculated indicator to the second calculation unit 130, and stores the processing result in the first storage unit 122 as necessary. Here, the indicator may be, for example, a likelihood ratio indicating the likelihood that a certain element belongs to a certain class among a plurality of classes. Alternatively, the indicator may be a function including the likelihood ratio as a variable. In the following description, it is assumed that the indicator is a likelihood ratio. The likelihood ratio calculated in Step S103 is used as an integrated score. After that, the process proceeds to Step S108. The process in Step S108 will be described later.

On the other hand, when there is past data in Step S102 (YES in Step S102), the process proceeds to Step S104. In Step S104, the indicator calculation unit 121 reads out the past data stored in the first storage unit 122. The first storage unit 122 stores, every time the indicator calculation unit 121 performs the processing, the processing result and the input element. In this storage process, new information may be overwritten on information stored in the past, or new information may be added while leaving information stored in the past. After that, the process proceeds to Step S105.

In Step S105, the indicator calculation unit 121 calculates, in consideration of two or more elements among the plurality of elements included in the sequential data, an indicator (likelihood ratio) indicating which one of the plurality of classes the input element should belong to. The two or more elements include the element that has been newly acquired and a previously processed element included in the past data. The first calculation unit 120 outputs the calculated indicator to the second calculation unit 130, and stores the processing result in the first storage unit 122 as necessary.

Note that the indicator calculation unit 121 extracts a feature from the element input from the sequential data. At this time, when there is no past data, the indicator calculation unit 121 performs feature extraction in consideration of the input element. On the other hand, when there is past data, the indicator calculation unit 121 performs feature extraction in consideration of the relationships between the input element and the past data. As a specific method of feature extraction, for example, a convolutional neural network (CNN) may be used, but the method is not limited thereto. As a specific method of storing the past data and calculating the relationship with current input data, for example, a long short term memory (LSTM) may be used, but the method is not limited thereto.

A specific example of the likelihood ratio will be described. The N (N is an integer equal to or larger than one) elements constituting the sequential data are expressed as $x_1, \ldots, x_N$, and the plurality of classes are expressed as $C_1$ and $C_2$. That is, in this example, for simplicity, it is assumed that the classification is two class classification in which the number of classes is two.

Here, when there is no past data (NO in Step S102), for example, a probability that the element $x_i$ (where i is any integer from 1 to N) belongs to the class $C_1$ is denoted by $p(x_i|C_1)$ and a probability that the element $x_i$ belongs to the class $C_2$ is denoted by $p(x_i|C_2)$. At this time, a likelihood ratio of them is expressed by the following Expression (1).

[Expression 1]

$$\frac{p(x_i|C_1)}{p(x_i|C_2)} \tag{1}$$

The likelihood ratio of Expression (1) indicates the ratio of likelihood between the probability that the element $x_i$ belongs to the class $C_1$ and the probability that the element $x_i$ belongs to the class $C_2$. When, for example, the likelihood ratio exceeds 1, since $p(x_i|C_1)>p(x_i|C_2)$, it is appropriate to classify the element $x_i$ into the class $C_1$ rather than the class $C_2$. As described above, the likelihood ratio of Expression (1) functions as an indicator indicating which one of the class $C_1$ or the class $C_2$ the input element should belong to.

Further, when there is past data (YES in Step S102), for example, the indicator calculation unit 121 can calculate the indicator in consideration of a plurality of elements, that is, a relationship between the input element and past data, as described above. In this case, for example, the likelihood ratio calculated in consideration of the two elements $x_i$ and $x_j$ (each of i and j is any integer from 1 to N, where i≤j) is expressed by the following Expression (2).

[Expression 2]

$$\frac{p(x_i, x_j|C_1)}{p(x_i, x_j|C_2)} \tag{2}$$

After the processing in Step S105, the process proceeds to Step S106. In Step S106, the weight calculation unit 131 reads out, from the first storage unit 122, the likelihood ratio calculated in the past. The weight calculation unit 131 calculates, using the likelihood ratio calculated this time by the indicator calculation unit 121 and the likelihood ratio calculated in the past, respective weights that correspond to the likelihood ratio calculated this time and the likelihood ratio calculated in the past. The second storage unit 132 stores the weights calculated by the weight calculation unit 131. The "weight" here is a value for adjusting a degree of influence that the likelihood ratio calculated this time and the likelihood ratio calculated in the past have on an integrated indicator that is newly calculated, and is calculated in accordance with the reliability of the element that has been newly acquired. The "reliability" is a degree of reliability regarding the calculation of a likelihood ratio. For example, the reliability of the element where an appropriate likelihood ratio is calculated becomes high and the reliability of the element where an inappropriate likelihood ratio is calculated becomes low.

The weight here may be, for example, an inner product $V_{ij} \cdot V_{iN}$ of a vector $V_{ij}$ having an element that is the probability that the input data belongs to each class, the vector $V_{ij}$ being calculated in consideration of the elements from the element $x_i$ to the element $x_j$ of the elements that constitute the sequential data, and a vector $V_{iN}$ having an element that is the probability that the input data belongs to each class, the vector $V_{iN}$ being calculated in consideration of the elements from the element $x_i$ to the element $x_N$ of the elements that constitute the sequential data. Each of the symbols i and j may be any integer from 1 to N. Note that i≤j. In the following description, it is assumed that the weight is obtained by the inner product.

The calculation of the weight is not limited to the calculation where the weight is obtained by the inner product. For example, an integrated indicator calculated in the past may be read out from the third storage unit 142, and this integrated indicator may be used to calculate the weight. After that, the process proceeds to Step S107.

In Step S107, the integrated indicator calculation unit 141 integrates the likelihood ratio calculated this time by the indicator calculation unit 121, the likelihood ratio calculated in the past, and the weight calculated this time by the weight calculation unit 131 to calculate a new integrated indicator.

The integrated indicator indicates which one of the plurality of classes the entire sequential data should belong to. The past integrated indicator means, when the current processing is processing for the j-th element in the sequential data, an integrated indicator calculated by the integrated indicator calculation unit 141 for an element before the j-th element. The past likelihood ratio means, when the current processing is processing for the j-th element in the sequential data, a likelihood ratio calculated by the indicator calculation unit 121 for an element before the j-th element. Note that the third storage unit 142 stores the integrated indicator every time the integrated indicator calculation unit 141 performs processing. In this storage processing, the value of the integrated indicator may be updated by overwriting the integrated indicator stored in the past with a new integrated indicator, or a new integrated indicator may be added while leaving the integrated indicator stored in the past.

The integrated indicator may be, for example, a sum of values obtained by multiplying all the calculated likelihood ratios including the past likelihood ratio by the weights that correspond to the respective likelihood ratios. In the following description, the sum of values obtained by multiplying the respective likelihood ratios by the corresponding weights is called an integrated score. Alternatively, the integrated indicator may be a function including the integrated score as a variable. In the following description, it is assumed that the integrated indicator is the integrated score.

Assuming that the number of classes is 2, a specific example of the integrated score will be described. When N elements are input at the time of calculating the integrated score, the N elements are expressed as $x_1, \ldots, x_N$. Here, the probability that the entire sequential data including the elements from the i-th element to the N-th element belong to the class $C_1$ is denoted by $p(x_i, \ldots, x_N|C_1)$. Further, the probability that the entire sequential data including the elements from the i-th element to the N-th element belong to the class $C_2$ is denoted by $p(x_i, \ldots, x_N|C_2)$. When $1 \le i \le N$ and $i=N$ are satisfied, the probability that data including only the N-th element belongs to the class $C_1$ is $p(x_N|C_1)$, and the probability that data including only the N-th element belongs to the class $C_2$ is $p(x_N|C_2)$. In this case, a likelihood ratio of them is expressed by the following Expression (3).

[Expression 3]

$$\frac{p(x_i, \ldots, x_N|C_1)}{p(x_i, \ldots, x_N|C_2)} \tag{3}$$

When only the likelihood ratio including elements from the first element to the N-th element of the sequential data is used as an integrated score as in a conventional SPRT, the integrated score is expressed by the following Expression (4).

[Expression 4]

$$\frac{p(x_1, \ldots, x_N|C_1)}{p(x_1, \ldots, x_N|C_2)} \tag{4}$$

However, as described above, in this example embodiment, the integrated score is calculated taking into consideration all the calculated likelihood ratios including the past likelihood ratio and importance of the respective likelihood ratios. Therefore, instead of using only one likelihood ratio as the integrated score, like in Expression (4), the integrated score is calculated by different calculation expressions depending on the number of all the calculated likelihood ratios including the past likelihood ratio.

When, for example, elements of the sequential data of up to the N-th element have been input, the integrated score can be calculated using the following Expression (5). The symbol i is an integer equal to or larger than one but equal to or smaller than N and j is an integer equal to or larger than i but equal to or smaller than N. Further, when i=j, the probability that data including only the i-th element belongs to the class $C_1$ is $p(x_i|C_1)$ and the probability that data including only the i-th element belongs to the class $C_2$ is $p(x_i|C_2)$. Further, $w_{ij}$ denotes a weight indicating the importance of each likelihood ratio, $w_{ij}$ being calculated by the weight calculation unit 131.

[Expression 5]

$$\sum_{j=1}^{N}\sum_{i=1}^{j} w_{ij}\frac{p(x_i, \ldots, x_j|C_1)}{p(x_i, \ldots, x_j|C_2)} \tag{5}$$

Specific examples of the weight will be described. It is assumed that the first to N-th elements $x_1, \ldots, x_N$ of the elements constituting the sequential data have been input and the plurality of classes are denoted by $C_1$ and $C_2$. That is, in this example, for simplicity, it is assumed that the classification is two-class classification in which the number of classes is two. Here, the probability that the sequential data including elements from the element $x_i$ to the element $x_j$ belongs to the class $C_1$ is denoted by $p(x_i, \ldots, x_j|C_1)$. Further, the probability that the sequential data including elements from the element $x_i$ to the element $x_j$ belongs to the class $C_2$ is denoted by $p(x_i, \ldots, x_j|C_2)$. Note that i is an integer equal to or larger than one but equal to or smaller than N and j is an integer equal to or larger than i but equal to or smaller than N. Further, when i=j, it is assumed that the probability that the data including only the i-th element belongs to the class $C_1$ is $p(x_i|C_1)$ and the probability that the data including only the i-th element belongs to the class $C_2$ is $p(x_i|C_2)$. When the vector having elements that are $p(x_i, \ldots, x_j|C_1)$ and $p(x_i, \ldots, x_j|C_2)$ is denoted by $V_{ij}$, the weight $w_{ij}$ in Expression (5) is the inner product $V_{ij} \cdot V_{iN}$ of $V_{ij}$ and $V_{iN}$. Accordingly, the weight that corresponds to the likelihood ratio in a case where the i-th element to the j-th element of the sequential data are taken into consideration becomes larger as the degree of similarity between the classification result in a case where the elements from the i-th element to the N-th element, which is the latest element, of the sequential data are taken into consideration and the classification result in a case where the elements from the i-th element to the j-th element of the sequential data are taken into consideration becomes larger. Accordingly, even in a case where the sequential data acquired in the past includes data that is inappropriate to determine data in a different class or the like, it is possible to reduce the influence of the likelihood ratio calculated in consideration of data that is inappropriate for the determination on the integrated score, and to improve the accuracy of the determination.

The method for calculating the weight is not limited to the aforementioned one. For example, a vector having elements that are probabilities $p(x_N|C_1)$ and $p(x_N|C_2)$ in consideration of only the latest element $x_N$ of the sequential data may be denoted by $V_N$ and an inner product of a vector $V_{ij}$ having elements that are $p(x_i, \ldots, x_j|C_1)$ and $p(x_i, \ldots, x_j|C_2)$ and the $V_N$ may be used as the weight $w_{ij}$ in Expression (5). In this case, in this weighting, the latest element $x_N$ of the sequential data is considered to be the most important. Further, in another example, a difference $V_{ij}-V_{ij-1}$ between the vector $V_{ij}$ and a vector $V_{ij-1}$ having elements that are $p(x_i, \ldots, x_{j-1}|C_1)$ and $p(x_i, \ldots, x_{j-1}|C_2)$ may be calculated and the absolute value of $V_{ij}-V_{ij-1}$ may be used as the weight $w_{ij}$ in Expression (5). In this case, in this weighting, data in a case where the newly input sequential data has changed significantly compared to the sequential data obtained one time ago is considered to be important. Note that, the method for calculating the weight is not limited thereto.

After the processing in which all the weights that can be calculated are calculated, processing of normalizing the weights may be performed. The method for normalization includes, for example, a method for using a Softmax function.

As the likelihood ratio shown in Expression (5), the likelihood ratio calculated by the indicator calculation unit 121 in advance in Step S103 may be used.

While Expression (5) shows examples of a case of two-class classification in which the likelihood ratio between the class $C_1$ and the class $C_2$ is calculated, the number of classes may be three or more. When, for example, the number of classes is M, Expression (5) can be extended so that the integrated score between the a-th class and all the classes other than the a-th class among the M classes can be calculated. An example of such extension is one using the maximum likelihood of all classes other than the a-th class as in the following Expression (6). In Expression (6), the m-th (m is any integer from 1 to M) class is denoted by $C_m$, a is any integer from 1 to M, and b may be any integer from 1 to M except a.

[Expression 6]

$$\sum_{i=1}^{N}\sum_{j=1}^{i} w_{ij} \frac{p(x_j, \ldots, x_N | C_a)}{\max_{b \neq a} p(x_j, \ldots, x_N | C_b)} \tag{6}$$

As another example, the sum of likelihoods of all the classes other than the a-th class is used as in the following Expression (7). In Expression (7), the m-th (m is any integer from 1 to M) class is denoted by $C_m$, a is any integer from 1 to M, and b may be any integer from 1 to M except a. The method for calculating the integrated score when the number of classes is three or more is not limited thereto.

[Expression 7]

$$\sum_{i=1}^{N}\sum_{j=1}^{i} w_{ij} \frac{p(x_j, \ldots, x_N | C_a)}{\sum_{b \neq a}^{M} p(x_j, \ldots, x_N | C_b)} \tag{7}$$

While Expressions (5) to (7) illustrate the case where all the elements from the first element to the N-th element of the input sequential data are used, the number of elements to be considered may be any number. For example, the maximum number of elements to be used P may be set in advance, and when the number of elements of the input sequential data exceeds P, only the P latter items of the sequential data may be taken into account. This prevents the computational load from becoming too high.

The method for calculating the integrated indicator is not limited to that described above. For example, the integrated indicator may be calculated by a method using LSTM or a deep neural network.

After the processing in Step S107, the process proceeds to Step S108. In Step S108, the classification unit 150 determines whether or not the sequential data can be classified into any one of the classes based on the integrated indicator calculated by the third calculation unit 140. When the integrated indicator is the integrated score, the classification unit 150 determines whether or not classification of a class is possible based on, for example, whether or not there is a class in which the integrated score exceeds a predetermined threshold. If classification is not possible (NO in Step S108), the process proceeds to Step S101, and the acquisition unit 110 acquires the next element. If classification is possible (YES in Step S108), the process proceeds to Step S109.

In Step S109, the classification unit 150 classifies the sequential data into one of the classes based on the integrated indicator. For example, when the integrated indicator is an integrated score, the sequential data is classified as belonging to a class in which the integrated score exceeds a predetermined threshold.

The processing in Steps S108 and S109 will be described in more detail with reference to a specific example. It is assumed that the classification processing in this example is two-class classification into the class $C_1$ or the class $C_2$, and thresholds for determination of the class $C_1$ and the class $C_2$ are $T_1$ and $T_2$, respectively. Further, the integrated score is denoted by L.

In this case, when $L>T_1$, the classification unit 150 classifies the sequential data into the class $C_1$, and the process ends. When $L>T_2$, the classification unit 150 classifies the sequential data into the class $C_2$, and the process ends. When $L \leq T_1$ and $L \leq T_2$, the classification unit 150 determines that classification is not possible, and the acquisition unit 110 acquires the next element.

When the number of classes is M that is three or more, M thresholds are prepared in the similar manner as described above, and a similar classification process can be performed by determining the magnitude relation between each of the M integrated scores and a corresponding threshold. At this time, the classification unit 150 classifies the sequential data into a class in which the integrated score first exceeds the threshold. When the integrated score does not exceed any threshold, the classification unit 150 determines that classification is not possible, and the acquisition unit 110 acquires the next element.

The classification method described above is an example and is not limited thereto. For example, when the number of elements input in Steps S107 and S108 is greater than a predetermined value (the maximum number of elements), the sequential data may be forcibly classified into any one of the classes even if there is no class in which the integrated score exceeds the threshold, and the process may be terminated. This can prevent the calculation time from becoming excessively long. In this example, it is desirable that the determination criteria be mutually exclusive so that the sequential data can be reliably classified into any class.

Specific examples of mutually exclusive criteria will be described. In the case of two-class classification, when the number of elements exceeds the maximum number of elements, it is possible to use a method of classifying the sequential data into one of two classes depending on whether the value of the integrated score L is 0 or more. In the case of M class classification, it is possible to use a method of classifying the sequential data into a class having the maximum value among the overall likelihood ratios corresponding to the respective classes.

As described above, according to this example embodiment, classification of sequential data is performed using the integrated indicator in which a plurality of elements of sequential data and the importance of the respective elements are considered. Thus, classification in accordance with a correlation length of the sequential data in which the property of the sequential data is taken into account may be performed, whereby the information processing apparatus 100 capable of accurately classifying sequential data is provided.

Second Example Embodiment

In this example embodiment, a medical image identification device 300 will be described as an application example of the information processing apparatus 100 according to the first example embodiment. Hereinafter, differences from the first example embodiment will be mainly described, and description of common parts will be omitted or simplified.

Figure 4:
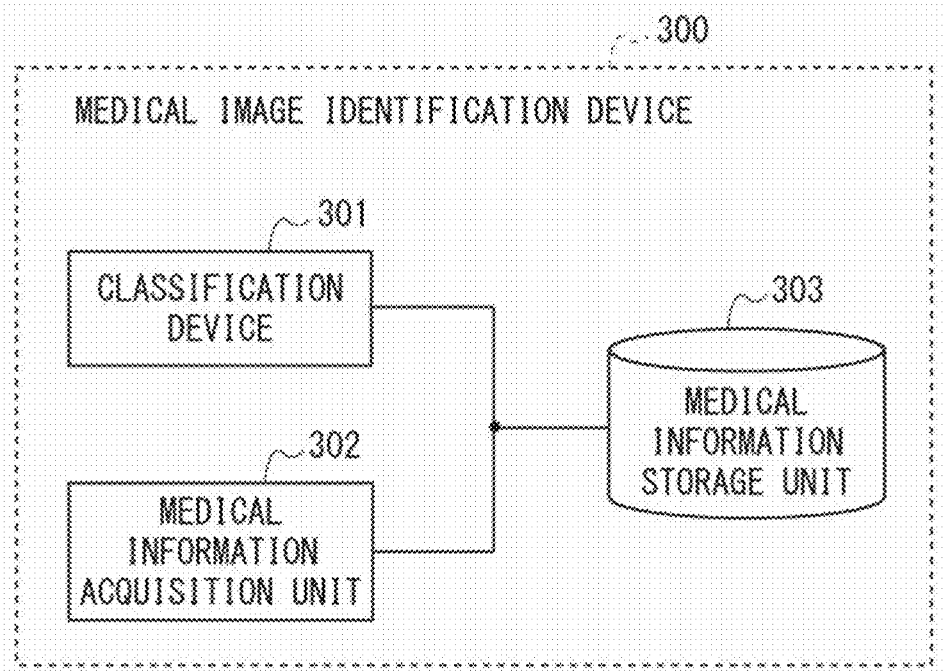
FIG. 4 is a functional block diagram of a medical image identification device, which is an application example of an information processing apparatus according to a second example embodiment.

FIG. 4 is a functional block diagram of the medical image identification device 300 according to the second example embodiment. The medical image identification device 300 includes a classification device 301, a medical information acquisition unit 302, and a medical information storage unit 303. The medical image identification device 300 may include a computer, just like the information processing apparatus 100 shown in FIG. 1. Therefore, description of the hardware configuration of the medical image identification device 300 will be omitted.

The medical image identification device 300 is, for example, a device for detecting cancer from medical information such as endoscopic images, CT images, or MRI images. The medical image identification device 300 may include a device (such as an endoscope system) for acquiring medical information, and may be operated in a stand-alone manner, or may acquire medical information from another device in a cancer detection system to detect cancer. Further, the medical image identification device 300 may be configured by a plurality of devices which are communicatively connected to each other.

The medical image identification device 300 may be, for example, an inspection device for cancer testing. Alternatively, the medical image identification device 300 may be an inspection device for aneurysm testing.

The medical information acquisition unit 302 is a device that acquires biometric information, and may be, for example, an endoscope system capable of capturing a moving image. In the identification of the medical information, a feature amount for matching may be extracted from an image or the like acquired by the medical information acquisition unit 302. This feature amount extraction processing may be performed in the classification device 301, may be performed in the medical information acquisition unit 302 at the time of acquiring the medical information, or may be performed by another device. In this specification, the image or the like acquired by the medical information acquisition unit 302 and the feature amount extracted therefrom may be collectively referred to as medical information.

The medical information storage unit 303 stores information necessary for processing in the classification device 301, such as medical information. The information processing apparatus 100 according to the first example embodiment is used as the classification device 301. The classification device 301 acquires the sequential data having elements that are the medical information as the sequential data described in the first example embodiment. The classification device 301 refers to the information stored in the medical information storage unit 303, and classifies the sequential data into one of a plurality of predetermined classes. Here, the plurality of classes may be, for example, classes each indicating the presence or absence of cancer. In other words, the plurality of classes may include, for example, a class indicating that a cancerous site exists in the input sequential data and a class indicating that a cancerous site does not exist in the input sequential data.

The medical image identification device 300 according to this example embodiment includes a classification device 301 capable of accurately classifying sequential data. Accordingly, a medical image identification device 300 that may perform cancer detection more appropriately is provided.

An example of cancer detection will be described as an example in which the feature of the information processing device 100 of the first example embodiment that the classification accuracy of the sequential data is high is utilized more in the medical image identification device 300 according to this example embodiment. One of methods for detecting cancer from medical video such as endoscopic video includes a method in which a probability that each image (frame) included in the video includes cancer is calculated by machine learning, the probability that corresponds to one input image or a weighted sum of the probability that corresponds to the number of images of a fixed length determined in advance is set as a score for classification, and it is determined that the image includes a cancerous site when the score for classification exceeds a threshold set in advance. The classification device 301 according to this example embodiment may receive a time-series image obtained by extracting a part of the medical video as the sequential data, and perform class classification indicating the presence or absence of a cancerous site of the sequential data using a luminance value of the image as a feature amount, whereby cancer may be detected.

A specific example in which cancer detection is actually performed from endoscopic video in the classification device 301 according to this example embodiment will be described below. In this specific example, data of the endoscopic video at a certain timing is regarded as the first element of the sequential data, elements from the first frame to the N-th frame at most are regarded as one sequential data item, and this sequential data is classified into a cancerous site or a non-cancerous site. Note that N is an integer equal to or larger than one.

First, in Step S101, one frame included in the endoscopic video is read out from the medical information acquisition unit 302 or the medical information storage unit 303.

Next, in Step S102, it is checked whether or not a past element of sequential data exists.

When there is no past element, the process proceeds to Step S103, where the likelihood ratio is calculated in consideration of only the elements of the input sequential data to obtain an integrated score.

When there is a past element, the process proceeds to Step S104, where the past element is read out, and the likelihood ratio in which the past data is taken into account and the weight that corresponds to the likelihood ratio are calculated, thereby calculating the integrated score in the procedure from Steps S104 to S107.

When the integrated score is compared with a threshold for determining the class and the integrated score exceeds the threshold for determining that the corresponding site is a cancerous site in Step S108, the sequential data is classified into video of a cancerous site in Step S109. Further, when the integrated score exceeds a threshold for determining that the corresponding site is a non-cancerous site, the sequential data is classified into video of a non-cancerous site in Step S109. When the aforementioned integrated score does not exceed thresholds of any class, the process returns to Step S101, where one frame included in the endoscopic video is newly acquired from the medical information acquisition unit 302 or the medical information storage unit 303.

In the above method, the input sequential data includes a cancerous site that can be easily determined, a cancerous site that is difficult to be determined, and a non-cancerous site. Further, the size of the cancer often varies for each medical image. The cancerous site that can be easily determined is, for example, a cancerous site that is elevated in a bumped shape. The cancerous site that is difficult to be determined is, for example, a flat cancerous site with no bumps or depressions. It is efficient that the cancerous site that is difficult to be determined be detected by using a plurality of images. Further, when the length of the sequential data is set large, the sequential data may include both a cancerous site and a non-cancerous site. In order to prevent the detection accuracy from decreasing due to the presence of data that should be classified into another class in the sequential data, it is effective that a weight be set in such a way that the importance of a likelihood ratio calculated from sequential data including an element that should be classified into a class that is different from that of the element currently acquired among the elements of the sequential data is reduced to reduce the influence of the likelihood ratio on an integrated score used for classification. Therefore, when classification for cancer detection is performed, it is effective to use classification processing of the information processing apparatus 100 according to the first example embodiment in which one or more elements of the sequential data are used in consideration of the importance of each element.

The device or system described in the above example embodiments can also be configured as in the following third example embodiment.

Third Example Embodiment

Figure 5:
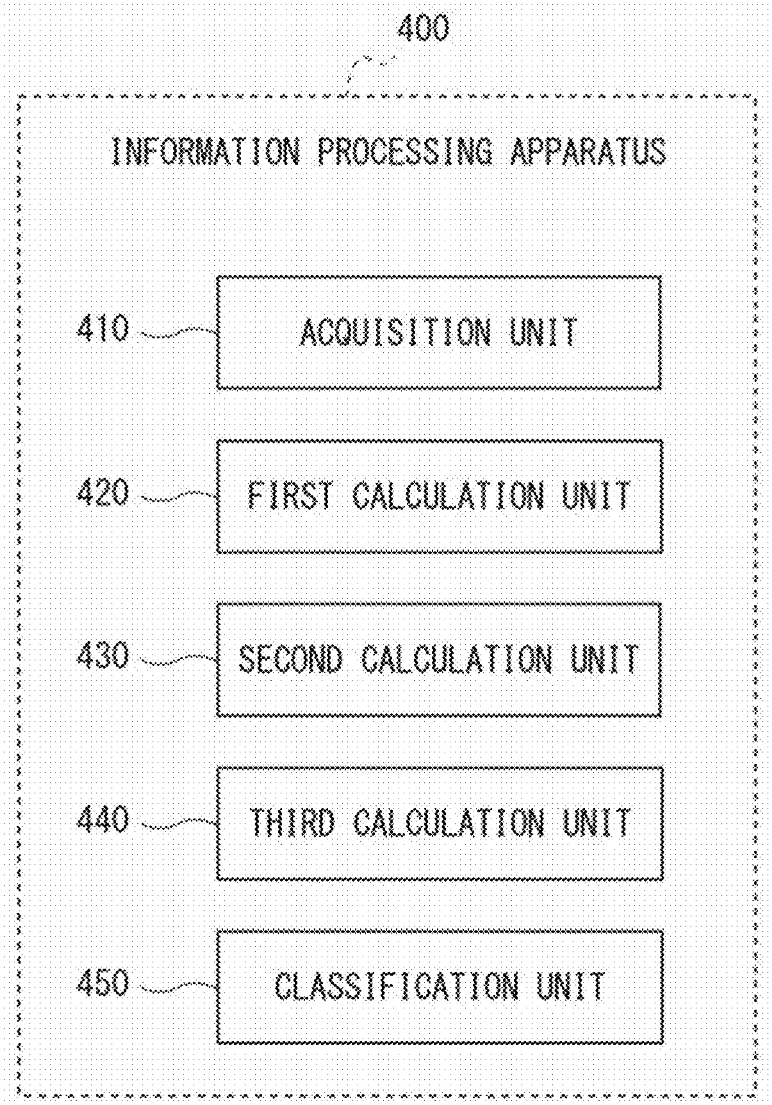
FIG. 5 is a functional block diagram of an information processing apparatus according to a third example embodiment.

FIG. 5 is a functional block diagram of an information processing apparatus 400 according to a third example embodiment. The information processing apparatus 400 includes an acquisition unit 410, a first calculation unit 420, a second calculation unit 430, a third calculation unit 440, and a classification unit 450. The acquisition unit 410 sequentially acquires a plurality of elements included in sequential data. The first calculation unit 420 calculates, in consideration of two or more of the plurality of elements, an indicator indicating which one of a plurality of classes each of a plurality of elements should belong to. The second calculation unit 430 calculates weights showing the importance of the indicators of the plurality of respective elements. The third calculation unit 440 weights the indicators of the plurality of respective elements with the corresponding weights and integrates the weighted indicators to calculate an integrated indicator indicating which one of a plurality of classes the sequential data should belong to. The classification unit 450 classifies the sequential data into any one of the classes based on the integrated indicator.

According to this example embodiment, the information processing apparatus 400 capable of accurately classifying sequential data is provided.

Other Example Embodiments

The present invention is not limited to the example embodiments described above, and may be suitably modified within the scope of the present invention. For example, an example in which a part of the configuration of one example embodiment is added to another example embodiment or an example in which a part of the configuration of one example embodiment is replaced with a part of the configuration of another example embodiment is also an example embodiment of the present invention.

The scope of each of the example embodiments also includes a processing method that stores, in a storage medium, a program that causes the configuration of each of the example embodiments to operate so as to implement the function of each of the example embodiments described above, reads the program stored in the storage medium as a code, and executes the program in a computer. That is, the scope of each of the example embodiments also includes a computer readable storage medium. Further, each of the example embodiments includes not only the storage medium in which the computer program described above is stored but also the computer program itself. Further, one or two or more components included in the example embodiments described above may be a circuit such as an application specific integrated circuit (ASIC) and a field programmable gate array (FPGA), configured to implement the function of each component.

As the storage medium, for example, a floppy (registered trademark) disk, a hard disk, an optical disk, a magneto-optical disk, a compact disk (CD)-ROM, a magnetic tape, a nonvolatile memory card, or a ROM can be used. Further, the scope of each of the example embodiments includes an example that operates on operating system (OS) to perform a process in cooperation with another software or a function of an add-in board without being limited to an example that performs a process by an individual program stored in the storage medium.

Further, a service implemented by the function of each of the example embodiments described above may be provided to a user in a form of software as a service (Saas).

It should be noted that the above-described embodiments are merely examples of embodying the present invention, and the technical scope of the present invention should not be limitedly interpreted by them. That is, the present invention can be implemented in various forms without departing from the technical idea or the main features thereof.

The whole or part of the example embodiments disclosed above can be described as, but not limited to, the following supplementary notes.

(Supplementary Note 1)

An information processing apparatus comprising:

acquisition means for sequentially acquiring a plurality of elements included in sequential data;

a first calculation means for calculating, based on two or more of the plurality of elements, indicators indicating which one of a plurality of classes the plurality of respective elements should belong to;

a second calculation means for calculating weights showing importance of the respective indicators of the plurality of respective elements;

a third calculation means for weighting the indicators of the plurality of respective elements by the corresponding weights and integrating the weighted indicators to calculate an integrated indicator indicating which one of the plurality of classes the sequential data should belong to; and classification means for classifying the sequential data into one of the classes based on the integrated indicator.

(Supplementary Note 2)

The information processing apparatus according to Supplementary Note 1, wherein the second calculation means calculates weights showing the importance of the respective indicators of the plurality of respective elements using one or more of the indicators including the indicators that correspond to the respective weights, the one or more of the indicators being calculated by the first calculation means.

(Supplementary Note 3)

The information processing apparatus according to Supplementary Note 1 or 2, wherein the second calculation means calculates weights showing the importance of the respective indicators of the plurality of respective elements using two or more of the indicators including the indicators that correspond to the respective weights, the two or more of the indicators being calculated by the first calculation means.

(Supplementary Note 4)

The information processing apparatus according to any one of Supplementary Notes 1 to 3, wherein the indicator includes a likelihood ratio indicating a likelihood that each of the plurality of elements belongs to a certain one of the plurality of classes.

(Supplementary Note 5)

The information processing apparatus according to any one of Supplementary Notes 1 to 4, wherein the integrated indicator includes an integrated score indicating a likelihood that the sequential data belongs to a certain one of the plurality of classes.

(Supplementary Note 6)

The information processing apparatus according to Supplementary Note 5, wherein, when there is a class in which the integrated score exceeds a predetermined threshold, the classification means classifies the sequential data into a class in which the integrated score exceeds the threshold.

(Supplementary Note 7)

The information processing apparatus according to Supplementary Note 5 or 6, wherein, when there is no class in which the integrated score exceeds a predetermined threshold, the classification means does not classify the sequential data into any class, and the acquisition means further acquires another element.

(Supplementary Note 8)

The information processing apparatus according to any one of Supplementary Notes 5 to 7, wherein, when there is no class in which the integrated score exceeds a predetermined threshold and the number of elements acquired by the acquisition means is greater than a predetermined value, the classification means classifies the sequential data into any one of the classes based on the integrated score.

(Supplementary Note 9)

The information processing apparatus according to any one of Supplementary Notes 1 to 8, wherein the first calculation means comprises:

a first storage means for storing at least the element acquired by the acquisition means in the past; and an indicator calculation means for calculating, when an element of the sequential data has been newly acquired by the acquisition means, the indicator for the element that has been newly acquired based on the element that has been newly acquired and the element that has been acquired in the past and is stored in the first storage means.

(Supplementary Note 10)

The information processing apparatus according to Supplementary Note 9, wherein the second calculation means comprises:

a second storage means for storing the indicator calculated in the past by the first calculation means; and weight calculation means for calculating, by using the indicator newly calculated by the first calculation means and the indicator that has been calculated in the past and is stored in the second storage means, the weights for the plurality of respective indicators that have been used.

(Supplementary Note 11)

The information processing apparatus according to Supplementary Note 10, wherein the third calculation means comprises integrated indicator calculation means for calculating the integrated indicator based on the indicator newly calculated by the first calculation means, the indicator that has been calculated in the past and is stored in the second storage means, and weights that correspond to the newly calculated indicator and the indicator calculated in the past, the weights being calculated by the weight calculation means.

(Supplementary Note 12)

The information processing apparatus according to any one of Supplementary Notes 1 to 11, wherein the sequential data is time-series data.

(Supplementary Note 13)

A medical image identification device comprising:

medical information acquisition means for acquiring medical information on a target person; and the information processing apparatus according to any one of Supplementary Notes 1 to 12, wherein the information processing apparatus classifies the sequential data including the medical information as the element into one of the classes.

(Supplementary Note 14)

The medical image identification device according to Supplementary Note 13, wherein the information processing apparatus classifies the sequential data into any one of the classes indicating the presence or absence of a cancerous site of the medical information.

(Supplementary Note 15)

An information processing method comprising the steps of:

sequentially acquiring a plurality of elements included in sequential data;

calculating, based on two or more of the plurality of elements, indicators indicating which one of a plurality of classes the plurality of respective elements should belong to;

calculating weights showing importance of the respective indicators of the plurality of respective elements;

weighting the indicators of the plurality of respective elements by the corresponding weights and integrating the weighted indicators to calculate an integrated indicator indicating which one of the plurality of classes the sequential data should belong to; and classifying the sequential data into one of the classes based on the integrated indicator.

(Supplementary Note 16)

A non-transitory computer readable medium storing a program for causing a computer to execute an information processing method comprising the steps of:

sequentially acquiring a plurality of elements included in sequential data;

calculating, based on two or more of the plurality of elements, indicators indicating which one of a plurality of classes the plurality of respective elements should belong to;

calculating weights showing importance of the respective indicators of the plurality of respective elements;

weighting the indicators of the plurality of respective elements by the corresponding weights and integrating the weighted indicators to calculate an integrated indicator indicating which one of the plurality of classes the sequential data should belong to; and classifying the sequential data into one of the classes based on the integrated indicator.

While the present invention has been described above with reference to the example embodiments, the present invention is not limited to the aforementioned example embodiments. Various changes that may be understood by one skilled in the art within the scope of the invention may be made to the configuration and the details of the present invention.

REFERENCE SIGNS LIST

100, 400 INFORMATION PROCESSING APPARATUS
101 PROCESSOR
102 MEMORY
103 STORAGE
104 INPUT AND OUTPUT I/F
105 COMMUNICATION I/F
110, 410 ACQUISITION UNIT
120, 420 FIRST CALCULATION UNIT
121 INDICATOR CALCULATION UNIT
122 FIRST STORAGE UNIT
130, 430 SECOND CALCULATION UNIT

131 WEIGHT CALCULATION UNIT
132 SECOND STORAGE UNIT
140, 440 THIRD CALCULATION UNIT
141 INTEGRATED INDICATOR CALCULATION UNIT
142 THIRD STORAGE UNIT
150, 450 CLASSIFICATION UNIT
201 DATA ACQUISITION DEVICE
202 INPUT DEVICE
203 DISPLAY DEVICE
300 MEDICAL IMAGE IDENTIFICATION DEVICE
301 CLASSIFICATION DEVICE
302 MEDICAL INFORMATION ACQUISITION UNIT
303 MEDICAL INFORMATION STORAGE UNIT

What is claimed is:

1. An information processing apparatus comprising:

at least one memory; and at least one processor coupled to the at least one memory, wherein the at least one processor sequentially acquires a plurality of elements included in sequential data;

the at least one processor calculates, based on two or more of the plurality of elements, indicators indicating which one of a plurality of classes the plurality of respective elements should belong to;

the at least one processor calculates weights showing importance of the respective indicators of the plurality of respective elements;

the at least one processor weights the indicators of the plurality of respective elements by the corresponding weights and integrating the weighted indicators to calculate an integrated indicator indicating which one of the plurality of classes the sequential data should belong to;

the at least one processor classifies the sequential data into one of the classes based on the integrated indicator;

the integrated indicator includes an integrated score indicating a likelihood that the sequential data belongs to a certain one of the plurality of classes; and when there is no class in which the integrated score exceeds a predetermined threshold, in the classification of the sequential data, the sequential data is not classified into any class, and in the acquisition of the plurality of elements, another element is acquired.

2. The information processing apparatus according to claim 1, wherein, in the calculation of the weights, weights showing the importance of the respective indicators of the plurality of respective elements are calculated using one or more of the indicators including the indicators that correspond to the respective weights, the one or more of the indicators being calculated in the calculation of the indicators.

3. The information processing apparatus according to claim 1, wherein, in the calculation of the weights, weights showing the importance of the respective indicators of the plurality of respective elements are calculated using two or more of the indicators including the indicators that correspond to the respective weights, the two or more of the indicators being calculated in the calculation of the indicators.

4. The information processing apparatus according to claim 1, wherein the indicator includes a likelihood ratio indicating a likelihood that each of the plurality of elements belongs to a certain one of the plurality of classes.

5. The information processing apparatus according to claim 1, wherein, in the classification of the sequential data, when there is a class in which the integrated score exceeds a predetermined threshold, the sequential data is classified into a class in which the integrated score exceeds the threshold.

6. The information processing apparatus according to claim 1, wherein, in the classification of the sequential data, when there is no class in which the integrated score exceeds a predetermined threshold and the number of acquired elements is greater than a predetermined value, the sequential data is classified into any one of the classes based on the integrated score.

7. The information processing apparatus according to claim 1, wherein the sequential data is time-series data.

8. A medical image identification device comprising:

a medical information acquisition apparatus configured to acquire medical information on a target person; and the information processing apparatus according to claim 1, wherein the information processing apparatus classifies the sequential data including the medical information as the element into one of the classes.

9. The medical image identification device according to claim 8, wherein the information processing apparatus classifies the sequential data into any one of the classes indicating the presence or absence of a cancerous site of the medical information.

* * * * *